United States Patent [19]

Fernholz et al.

[11] 4,092,267
[45] May 30, 1978

[54] PROCESS FOR REGENERATING PALLADIUM CATALYSTS

[75] Inventors: Hans Fernholz, Fischbach, Taunus; Hans Krekeler, Bad Wiessee; Hans-Joachim Schmidt, Falkenstein, Taunus; Friedrich Wunder, Florsheim (Main) all of Germany

[73] Assignee: Hoechst Aktiengesellschaft, Frankfurt, Germany

[21] Appl. No.: 669,484

[22] Filed: Mar. 23, 1976

[30] Foreign Application Priority Data

Mar. 25, 1975 Germany .............................. 2513125

[51] Int. Cl.² .................... B01J 23/96; B01J 31/40; C07C 67/05
[52] U.S. Cl. .................................. 252/413; 252/414; 260/410.9 M; 560/245
[58] Field of Search ...................... 252/413, 414, 412; 260/497 A; 560/245

[56] References Cited

U.S. PATENT DOCUMENTS

| | | | |
|---|---|---|---|
| 3,260,739 | 7/1966 | Schaeffer | 260/497 A |
| 3,290,362 | 12/1966 | Schaeffer | 260/497 A |
| 3,592,840 | 7/1971 | Durstom | 252/413 |
| 3,686,287 | 8/1972 | Knights | 260/497 A |

FOREIGN PATENT DOCUMENTS

| | | | |
|---|---|---|---|
| 708,198 | 4/1965 | Canada | 252/413 |
| 1,016,626 | 1/1966 | United Kingdom | 252/413 |

*Primary Examiner*—Winston A. Douglas
*Assistant Examiner*—P. E. Konopka
*Attorney, Agent, or Firm*—Curtis, Morris & Safford

[57] ABSTRACT

Process for regenerating palladium carrier catalysts for the oxacylation of olefins in the gaseous phase by treating the exhausted catalyst with a fatty acid blended with nitric oxides, nitric acid, peroxides or per-acids, by subsequent drying at temperatures below 90° C and evaporation of the fatty acid to a residual content of below 8 weight %.

9 Claims, No Drawings

PROCESS FOR REGENERATING PALLADIUM CATALYSTS

The present invention is related to a process for regenerating palladium carrier catalysts which are used for the oxacylation of olefins in the gaseous phase, especially for the preparation of vinyl acetate from ethylene or of allyl acetate from propylene, acetic acid and oxygen. Such catalysts quite frequently show a gradual loss of activity with a prolonged use. Oxacylation catalysts of this kind have been described so far quite often. Prior to use, the fundamental difference of the various types is the fact that one type contains palladium in its zero-valent or elementary stage, whilst other types contain the palladium in its bivalent stage as a salt or a compound. Both types may be regenerated according to the process of the invention.

The catalysts are especially appropriate for the oxacylation of olefins $C_nH_{2n}$ having from 2 to 12 carbon atoms, preferably from 2 to 4 carbon atoms, by reaction with unsubstituted saturated aliphatic monocarboxylic acids having up to 10 carbon atoms and being vaporizable under the reaction conditions. Preference is given to the use of unsubstituted saturated aliphatic monocarboxylic acids having from 2 to 5 carbon atoms, i.e. acetic acid, propionic acid, n-butyric acid and isobutyric acid or the various valeric acids.

Suitable catalyst carriers are all inert substances which do not lose their mechanical stability under the exacylation conditions. Such suitable carriers are, for example, silicic acid, silica gel, silicates, alumosilicates, activated charcoal, aluminum oxide, spinels, zirconium oxide, pumice, and silicon carbide. The physical properties of the catalyst carriers may differ widely. A suitable carrier material is, for example, a silicic acid with a surface of from 40 to 300 mm$^2$/g and an average pore radius of from 50 to 2000 A.

Suitable palladium compounds are all salts and complex compounds thereof which are soluble and reducible and which do not deposit in the catalyst when ready for use any deactivating substances such as halogen or sulfur. Especially suitable are the palladium carboxylates, preferably the salts of aliphatic monocarboxylic acids having from 2 to 5 carbon atoms, such as acetate, propionate or butyrate. Also appropriate are e.g. palladium nitrate, palladium nitrite, palladium oxide-hydrate, palladium oxalate, palladium succinate, palladium benzoate, palladium salicylate, palladium tropolonate, palladium acetyacetonate, palladium-aceto-acetate. However, compounds such as palladium sulfate and the halides of palladium may be employed as well, provided that care be taken to eliminate prior to impregnation, the sulfate ion, e.g. by precipitation with barium acetate, or the halogen ion, e.g. by precipitation with silver nitrate, so that no sulfate ion or halogen ion can contact the carrier. Preference is given to the use of palladium acetate because of its solubility and accessibility.

The catalyst generally contains from 0.5 to 5 weight% of palladium, the metal ratio being calculated on the total mass of the carrier catalyst.

The carrier of the catalyst may be impregnated in such a way that the carrier substance is covered with the solution of the palladium compound, the excess solution being then poured off or filtered off. Suitable solvents are e.g. carboxylic acids which may also contain water.

The solution which is employed for impregnating the catalyst carrier, preferably contains, in addition to the palladium compound, salts and compounds of other metals which act as activating agents, promoting agents or co-catalysts. Activating or co-catalyzing additives for oxacylation of olefins are, for example, alkali metal carboxylates and alkaline earth metal carboxylates, such as potassium acetate, sodium acetate, lithium acetate, sodium propionate, potassium isobutyrate, magnesium acetate; also suitable are those alkali metal or alkaline earth metal compounds which are converted to carboxylates under the reaction conditions, such as hydroxides, oxides, carbonates. Further appropriate additives for activation or co-catalyzation are also salts, compounds and complex compounds of cadmium, bismuth, copper, manganese, iron, cobalt, cerium, vanadium, uranium, which do not contain any halogen or sulfur, e.g. carboxylates, oxides, hydroxides, carbonates, citrates, tartrates, nitrates, acetylacetonates, benzoylacetonates, acetoacetates. Especially suitable are cadmium acetate, bismuth acetate, copper acetylacetonate, iron citrate. Mixtures of various additives may be used as well. Each activator is generally added in such an amount that the activating agent contains the metal in a ratio of from 0.01 to 4 weight %, calculated on the total mass of the carrier catalyst.

The afore-mentioned palladium carrier catalysts may be employed for the oxacylation process either in reduced form or unreduced.

Generally, the oxacylation process is carried out by conducting carboxylic acid, olefin and oxygen or oxygen-containing gases at temperatures of from 100° to 250° C, preferably at 120° to 220° C, and under pressures of from 1 to 25 bars, preferably from 1 to 20 bars, over the prepared catalyst, componets have not been converted in the reaction may be recycled. It is advantageous to choose the concentration ratios in such a way that the reaction mixture is maintained outside the range determined by the known explosion limits. Most usefully, the oxygen concentration is kept low, for example below 8% by volume (calculated on the gaseous mixtures free from acetic acid) when using ethylene. Under certain conditions, a dilution with inert gases such as nitrogen or carbon dioxide may also be advantageous. $CO_2$ is especially suitable for use in circulation processes, since it is formed in small quantities during the reaction.

Processes for regenerating palladium metal carrier catalysts have been previously described several times. The catalyst regeneration as per German "Offenlegungsschrift" No. 2,420,374 — for example — requires the following processing steps:

a. a used palladium metal carrier catalyst is washed and impregnated with diluted hydrochloric acid containing a small portion of hydrazine, b. the washed catalyst is partially dried to a residual humidity of from 65 to 95%.

c. the catalyst still wet is treated with gaseous chlorine, d. humid air is conducted over the catalyst, e. the chlorinated catalyst is treated with an aqueous alkaline reducing solution, f. the thus obtained reduced catalyst is washed with an aqueous solution and g. dried.

This process has the advantage that the time-consuming and costly separation of the noble metals from the catalyst carrier is avoided, but it is disadvantageous on an industrial-technical scale due to the seven separate steps required for its execution. Similar statements are true for other regeneration processes described in the past.

The subject of the present invention is a process for regenerating palladium carrier catalysts which are used for the oxacylation of olefins in the gaseous phase and contain no other noble metal besides palladium, which comprises treating the exhausted palladium carrier catalyst with a mixture consisting of a fatty acid that is liquid under normal conditions as a first component and, as a second component, nitric oxides, optionally with the addition of oxygen or oxygen-containing gases, nitric acid, peroxides, or peracids, drying the treated catalyst at a temperature below 90° C and evaporating the fatty acid to a residual content of below 8 weight %.

Suitable fatty acid components of the regeneration mixture are e.g. the aliphatic monocarboxylic acids which have been specified above as starting products of the oxacylation reaction. Preference is given to the use of acetic acid.

Suitable per-acids are peracetic acid, perpropionic acid, perbutyric acid, pervaleric acid, etc. — i.e. generally the per-acids derived from carboxylic acids. A preferred second component of the regeneration mixture is nitric acid.

For catalysts with heavier losses of activity possibly due to the formation of inactive oxides of the palladium, it might be advantageous to reduce the used catalyst prior to its regeneration by conducting hydrogen over the catalyst at a temperature of from 100° to 200° C.

A palladium carrier catalyst having been regenerated by the process of the invention displays the same level of activity as a recently prepared fresh catalyst — under identical test conditions. Surprisingly, the process of the invention does not lead to a modification or shifting of the distribution of substances acting as activating agents, promoting agents or co-catalysts.

For carrying out the process in accordance with the invention, the exhausted carrier catalyst is impregnated with the regeneration mixture. To avoid waste of the solution and redistribution of the substances contained in the catalyst it is recommended to use a quantity of regeneration mixture or solution corresponding to the pore volume of the carrier catalyst. The impregnation may be carried out either in the liquid phase or by condensation of a vapor phase regeneration mixture on the carrier material. It is advantageous for the regeneration to maintain the impregnated carrier catalyst at a temperature of from 40° to 100° C for a period of at least 10 hours. Impregnation and regeneration may take place in the same vessel.

The use of regeneration mixtures, the fatty acid portion of which predominates, is advantageous. Generally, the fatty acid contains from 0.1 to 20 weight %, preferably from 1 to 10 weight % of the other component.

Drying is advantageously carried out under reduced pressure. It is furthermore recommended that the drying process be performed with an inert gas stream, e.g. nitrogen or carbon dioxide, especially in case of operation under normal or elevated pressure.

The process of the invention provides many advantages. Besides the fact that the costly separation of the active substances from the carrier material can be avoided, the regeneration according to the invention can be carried out not only outside the acyloxylation reactor, but also within the reactor, so that there is no more need to discharge the exhausted catalyst from the reactor, a time-consuming and costly step.

The following examples illustrate the invention:

EXAMPLE 1

A solution of 7.5 ml of concentrated nitric acid in 350 ml of acetic acid is poured over 1 liter (corresponding to a weight of about 600 g) of silicic acid catalyst containing 2.1% of palladium, 1.7% of cadmium, 1.9% of potassium and 0.07% of manganese in the form of acetates (the percentages indicated referring to the elements), the efficiency of which had fallen from 840 g of vinyl acetate per liter and hour to 430 g during oxacylation, and the whole is mixed quickly and thoroughly. The entire liquid is absorbed by the catalyst. The wet catalyst is stored in a loosely closed vessel at 80° C for 24 hours, then dried at 200 mm Hg and 60° C in a nitrogen stream to an acetic acid content of 1.2%.

The thus regenerated catalyst displays under the usual test conditions (from 175° to 180° C, 8 to 9 atmospheres, feed mixture per liter and hour: 1500 g of acetic acid, 2550 Nl of ethylene, 200 Nl of oxygen) a space-time yield of 855 g of vinyl acetate per liter and hour.

EXAMPLE 2

4.5 liters of the catalyst specified in example 1 having been partially deactivated during the oxacylation are sprayed with a solution of 1360 ml of acetic acid and 34 ml of concentrated nitric acid, while mixing constantly and thoroughly. The treatment is continued as in example 1.

Space-time yield of the catalyst: 860 g of vinyl acetate per liter and hour.

EXAMPLE 3

1 liter of the exhausted catalyst as specified in example 1 is heated to 80° C in a tube. An air stream saturated with acetic acid at 70° C is introduced until 360 ml of acetic acid have condensed on the catalyst. Nitric oxides are then blended into the air current until 3.5 Nl of nitric oxides have been absorbed. After 3 days at 80° C the catalyst is dried in the nitrogen current at 400 mm Hg and at 60° C to a content of acetic acid of 1.6%. Its space-time yield amounts to 845 g of vinyl acetate per liter and hour.

EXAMPLE 4

1 liter of a catalyst containing 1.8% of palladium, 0.8% of bismuth and 2% of potassium (as acetates, the percentages referring to the elements), the space-time yield of which had fallen during the oxacylation from 750 g of allyl acetate per liter and hour to 380 g, is impregnated with a mixture of 350 ml of butyric acid and 7.5 ml of concentrated nitric acid and maintained at 80° C for 10 hours. Subsequently, drying is carried out as in example 1 until 1.6% of residual butyric acid remain.

The thus regenerated catalyst displays under the usual acetoxylation conditions a space-time yield of 740 g of allyl acetate per liter and hour.

EXAMPLE 5

1 liter of a silicic acid catalyst consisting of 1.8% of palladium and 0.9% of vanadium (both originally applied as acetyl-acetonates) and 2% of potassium (originally applied as acetate) (the percentages referring to the elements), the space-time yield of which had fallen during oxacylation from 680 g of allyl acetate per liter and hour to 180 g, is reduced at 180° C by means of a mixture of 10% by volume of hydrogen and 90% by volume of nitrogen. The catalyst is then impregnated with a mixture of 310 ml of acetic acid and 55 ml of a 30% hydrogen peroxide which had been maintained previously at 40° C for 10 hours. The wet catalyst is then maintained at 60° C for 5 days and dried according to example 1.

The space-time yield of the thus regenerated catalyst amounts to 650 g of allyl acetate per liter and hour.

What is claimed is:

1. A process for regenerating palladium carrier catalysts which have been utilized for the oxacylation of olefins in the gaseous phase and which contain no noble metal other than palladium, which comprises impregnating a body of the used palladium carrier catalyst containing 0.5 to 5% of palladium and in solid form with a liquid mixture consisting essentially of 80 to 99.9% by weight of a first component which is a normally liquid fatty acid and 0.1 to 20% by weight of a second component selected from nitric oxides, nitric acid, peroxides, and per-acids, said liquid mixture being used in an amount such that it is substantially completely absorbed by the solid catalyst body, drying the catalyst at a temperature below 90° C. and evaporating the fatty acid to a residual content of below 8% by weight.

2. Process according to claim 1, wherein said first component is an unsubstituted, saturated aliphatic monocarboxylic acid having up to 10 carbon atoms.

3. Process according to claim 1, wherein said second component is nitric acid.

4. Process according to claim 1, wherein said mixture consists of 90 to 99 weight % of said fatty acid and from 1 to 10 weight % of said second component.

5. Process according to claim 1, wherein the drying step is carried out under reduced pressure.

6. Process according to claim 1, wherein the drying step is carried out in an inert gas stream.

7. Process according to claim 1, wherein the catalyst is regenerated in the reactor for the oxacylation.

8. A process according to claim 1, wherein said second component is a mixture of a nitric oxide and oxygen or an oxygen-containing gas.

9. A process according to claim 1, wherein the impregnating liquid mixture is used in an amount approximately equal to the pore volume of the catalyst.

* * * * *